United States Patent [19]

Campbell et al.

[11] 4,247,481
[45] Jan. 27, 1981

[54] CATALYST PASSIVATION IN PRODUCTION OF AMINES

[75] Inventors: Charles R. Campbell, Pensacola, Fla.; Charles E. Cutchens, Decatur, Ala.

[73] Assignee: Monsanto Company, St. Louis, Mo.

[21] Appl. No.: 106,587

[22] Filed: Dec. 26, 1979

[51] Int. Cl.$^3$ .................. C07C 85/12; C07C 85/11; C07C 85/26
[52] U.S. Cl. .......................... 564/492; 252/477 Q
[58] Field of Search ........... 260/583 K, 583 P, 570.9, 260/580, 575; 252/477 Q

[56] References Cited

U.S. PATENT DOCUMENTS

| | | | |
|---|---|---|---|
| 3,821,305 | 6/1974 | Bartalini et al. | 260/583 K |
| 4,176,092 | 11/1979 | Birkenstock et al. | 252/477 Q X |

FOREIGN PATENT DOCUMENTS 53-36442 10/1978 Japan .................. 260/583 P

Primary Examiner—John Doll
Attorney, Agent, or Firm—Thomas Y. Awalt, Jr.

[57] ABSTRACT

This is an improvement in a process for the production of an amine such as hexamethylenediamine from a nitrile such as adiponitrile where the nitrile is hydrogenated under pressure in the presence of a Raney nickel catalyst, the reaction being conducted in a reactor from which is discharged a product stream containing both the amine and the Raney nickel catalyst. The improvement comprises charging to the process discharge stream containing the product amine and the Raney nickel catalyst, a nitroaromatic compound, whereby the Raney nickel catalyst is passivated and catalytic decomposition of the amine is substantially decreased.

16 Claims, 1 Drawing Figure

U.S. Patent  Jan. 27, 1981  4,247,481
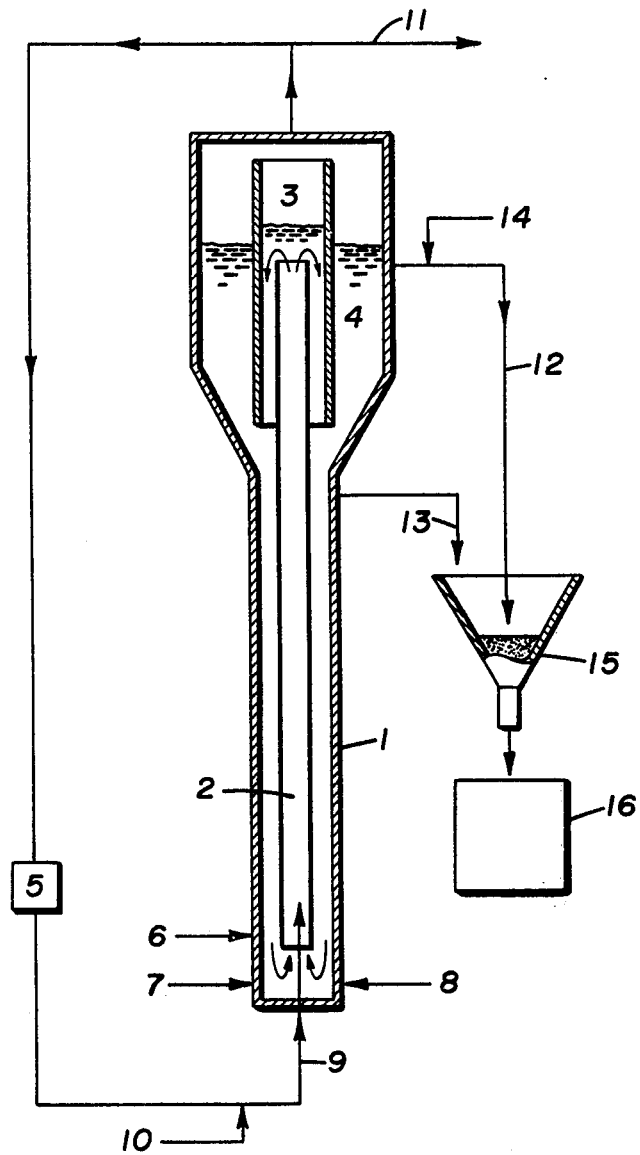

CATALYST PASSIVATION IN PRODUCTION OF AMINES

FIELD OF THE INVENTION

The invention relates to a process for the production of an amine such as hexamethylenediamine from a nitrile such as adiponitrile where the nitrile is hydrogenated under pressure in the presence of a Raney nickel catalyst, the reaction being conducted in a reactor from which is discharged a product stream containing both the amine and Raney nickel catalyst.

BACKGROUND OF THE INVENTION

It is well known that amines such as hexamethylenediamine can be produced by the catalytic hydrogenation of nitriles such as adiponitrile in the presence of Raney catalysts.

One such process is described in U.S. Pat. No. 3,821,305, in which hydrogenation is conducted in liquid phase at pressures of from 20–50 atmospheres and temperatures of 60°–100° C. in the presence of finely divided Raney catalyst and an inorganic base. Hydrogen and adiponitrile are fed into a liquid reaction medium consisting of hexamethylenediamine, water, the inorganic base, and the catalyst, in which medium the content of base is maintained in the range of 0.2–12 moles per kilogram of catalyst, while the content of water is maintained in the range of 2–130 moles per mole of the base.

The process discharge stream in the above described process contains both Raney catalyst and the product hexamethylenediamine, from which it is desirable to recover substantially pure hexamethylenediamine by distillation, and to recycle the Raney catalyst.

During such separation procedures, the crude amine is exposed to the Raney nickel catalyst under conditions favoring its decomposition or dehydrogenation. This decomposition is substantial if the catalyst is not separated or passivated immediately after the process discharge exits the reactor. Even the small amount of catalyst that normally gets through most commercial processes for removing catalyst (centrifuge, decantation, filtration) result in significant decomposition of amine if the catalyst is not passivated.

The substantial elimination of such decomposition would constitute a significant improvement in the art and is an object of this invention.

SUMMARY OF THE INVENTION

Briefly, the invention is an improvement in a process for the production of an amine such as hexamethylenediamine from a nitrile such as adiponitrile where the nitrile is hydrogenated under pressure in the presence of a Raney nickel catalyst continuously in a reactor thereby to produce an amine which is discharged in a stream from which is recovered both hexamethylenediamine and Raney nickel catalyst. The improvement comprises charging to the process discharge stream containing the product amine and the Raney nickel catalyst a nitroaromatic compound whereby the Raney nickel catalyst is passivated and catalytic decomposition of the amine is substantially decreased.

Any nitroaromatic compound may be employed except those containing functional groups which may react with the amine or tend to activate the Raney nickel catalyst. Nitrobenzene, dinitrobenzenes and dinitrophenols have been demonstrated effected. Dinitrophenols are preferred.

DETAILED DESCRIPTION OF THE INVENTION

The process for the production of the amine is preferably carried out in pressures from 20–50 atmospheres in temperatures from 60°–100° C., by feeding molecular hydrogen and adiponitrile into a liquid reaction medium containing, along with the hexamethylenediamine produced, water, sodium hydroxide and a finely divided Raney catalyst dispersed in the liquid components of the reaction medium. The catalyst, which may be Raney nickel, or Raney nickel containing small amounts of other metals such as chromium, loses all or most of its activity during hydrogenation. In order to maintain a given level of catalytic activity within the catalytic mass, it is necessary for the catalyst in the reaction medium to be gradually replaced. This replacement is effected by feeding fresh catalyst to the reaction vessel and removing a quantity of reaction medium which contains an amount of catalyst equal to that supplied. The fed catalyst may consist of a mixture of fresh catalyst and of recycled catalyst. Recycled catalyst is catalyst that has been washed prior to re-use.

The reaction medium preferably contains:

(1) a quantity of catalyst in excess of 1 part, by weight, per 100 parts of liquid reaction medium (hexamethylenediamine, water and sodium hydroxide), the upper limit depending solely on the fluidity of the reaction medium; the preferred range is from 3 to 35 parts per 100 parts by weight of the liquid reaction medium;

(2) a quantity of sodium hydroxide in the range of 0.2 to 12 moles per kilogram of catalyst and preferably between 1 and 3 moles per kilogram of catalyst;

(3) a quantity of water in the range of 2 to 130 moles per mole of sodium hydroxide and preferably between 7 and 70 moles per mole of sodium hydroxide.

Substantially similar results in the production of the amine can be obtained by using, instead of sodium hydroxide, a hydroxide of any other of the alkali metals. Throughout the following description, however, reference will be made to the preferred sodium hydroxide.

The liquid part of the reaction medium, under the starting conditions already specified, and within the preferred range of ratio of water to sodium hydroxide, consists of two phases. One phase, amounting to 0.5–5.0 parts per 100 parts of the other phase, consists of an aqueous solution of sodium hydroxide whose concentration is in the range of 25 to 55 percent by weight. The other phase consists of hexamethylenediamine containing water and small amounts of sodium hydroxide. The aqueous solution of sodium hydroxide, which is the heavier phase, contains most of the catalyst.

The equipment for continuous operation of the process is of conventional type. An example of this, which is not limitive of the invention, is shown in the accompanying drawing.

The equipment consists essentially of a vertical tubular reaction vessel, 1, provided inside with an injection device, 2, such as to promote the agitation of the reaction medium resulting from the hydrogen flow, and at the top with other devices, 3 and 4, which enable the separation of the gas from the liquid and the drawing off from the reaction vessel of a hydrogenated product having a low content of catalyst thus making it possible to maintain in the reaction vessel relatively high concentrations of catalyst—for example, 10 and 20 parts of catalyst per 100 parts by weight of liquid reaction medium.

The equipment also includes a gas re-cycling pump, 5, and pipes for feeding the reaction vessel with adiponitrile, 6, aqueous suspension of catalyst, 7, aqueous solution of sodium hydroxide, 8, and hydrogen, 9. The hydrogen consumed is replaced by feeding fresh hydrogen through pipe 10.

Part of the gas is vented through pipe 11, the purpose of this release being to maintain the hydrogen content in the re-cycled gas above a given value.

The output of clarified hexamethylenediamine is discharged through pipe 12.

Pipe 13 is used for removing an amount of reaction medium whose catalyst content is equivalent to the amount supplied through pipe 7. In this way, the concentration of catalyst in the reaction medium remains constant.

According to the present invention the nitroaromatic compound is introduced through pipe 14. The Raney nickel catalyst contained in the product discharge stream is collected at filter 15, and the pure hexamethylenediamine is collected in container 16.

While the nitroaromatic compound is preferably added as close to the reactor discharge point as possible, it can, of course, be added at any point downstream from the reactor in order to deactivate the catalyst.

Any amount of nitroaromatic compound (N) added to the process discharge stream will cause some deactivation of the catalyst, and lessen, to a certain extent, the catalytic decomposition of hexamethylenediamine. At a level of 2/1 N/catalyst weight ratio, catalyst passivation is significant. At a N/catalyst weight ratio of 10, catalyst activity is essentially eliminated, and there is little, if any, decomposition of the hexamethylenediamine. The preferred weight ratio range is 2–10.

EXAMPLES

In each example, reactor was charged with 70 grams hexamethylenediamine (HMD), and the amount shown of catalyst in an aqueous slurry. The nitroaromatic compound was added so as to provide a weight ratio as shown. A nitrogen blanket was applied and the reactor held at 50° C. (isothermal) for two hours. The reaction mix was then refluxed at atmospheric pressure for five hours. A sample of the reaction mix was then analyzed. The initial charge and the results of analysis are shown at Table 1 where:

HMI = hexamethyleneimine
ACH = azacycloheptene-1
HMD = hexamethylenediamine
ADN = adiponitrile
BHMT = bis-hexamethylenetriamine Under these conditions when no activating agent is added, about 30% of the hexamethylenediamine is decomposed as shown by Examples 1 and 2.

This data shows a correlation between concentration of nitro functionality and extent of catalyst deactivation. All of the nitro-containing compounds are considered as potential deactivating agents. However, the relatively low solubility of nitrobenzene and dinitrobenzene in aqueous hexamethylenediamine tends to reduce their effectiviness as passifiers.

TABLE 1

| Example | Additive Name | Additive GMS | CAT. GMS | HMI | ACH | HMD | ACN | ADN | BHMT | UNKS | PRI,mpm |
|---|---|---|---|---|---|---|---|---|---|---|---|
| 1* | No additive | 0 | 0.5 | 7.5 | 7.3 | 71.0 | 6.1 | .52 | 5.8 | 1.8 | 186,800 |
| 2* | No additive | 0 | 0.5 | 10.8 | 7.0 | 67.6 | 5.8 | .76 | 6.0 | 2.3 | 187,000 |
| 3 | Nitrobenzene | 0.3 | 0.5 | 10.6 | 6.2 | 67.4 | 6.3 | 0.53 | 5.8 | 3.4 | 243,000 |
| 4 | Nitrobenzene | 1.1 | 0.5 | 7.6 | 3.5 | 75.6 | 5.3 | 0.61 | 3.2 | 4.4 | 176,000 |
| 5 | M-dinitrobenzene | 1.1 | 0.5 | 6.2 | 2.9 | 84.0 | 2.5 | 0.44 | 1.9 | 2.2 | 103,000 |
| 6 | M-dinitrobenzene | 2.1 | 0.5 | 4.4 | 2.7 | 87.8 | 1.2 | 0.32 | 1.2 | 2.3 | 68,400 |
| 7 | 2,4 dinitrophenol | 1.1 | 0.5 | 4.3 | 1.9 | 87.1 | 2.3 | 0.30 | 1.4 | 1.1 | 58,700 |
| 8 | 2,4 dinitrophenol | 5.0 | 0.5 | 0.03 | 3.0 | 93.1 | 0.20 | 0.04 | <0.1 | 0.26 | 12,400 |

*comparative

We claim:

1. In a process for the production of an amine from a nitrile where the nitrile is hydrogenated under pressure in the presence of a Raney nickel catalyst continuously in a reactor thereby to produce the amine which is discharged in a stream from which is recovered both the amine and Raney nickel catalyst, the improvement comprising charging to the process discharge stream comprising the product amine and Raney nickel catalyst a nitroaromatic compound whereby the Raney nickel catalyst is passivated and catalytic decomposition of the amine is substantially decreased.

2. The process improvement of claim 1 wherein the weight ratio of the nitroaromatic compound to the catalyst is about 2–10.

3. The process improvement of claim 1 wherein the weight ratio of the nitroaromatic compound to the catalyst is about 10.

4. The process improvement of claim 1 wherein the nitroaromatic compound is selected from the group consisting of nitrobenzene, dinitrobenzene and dinitrophenol.

5. The process improvement of claim 1 wherein the nitroaromatic compound is 2,4-dinitrophenol.

6. In a process for the production of hexamethylenediamine from adiponitrile where the adiponitrile is hydrogenated under pressure in the presence of a Raney nickel catalyst continuously in a reactor thereby to produce hexamethylenediamine which is discharged in a stream from which is recovered both hexamethylenediamine and Raney nickel catalyst, the improvement comprising charging to the process discharge stream comprising the product hexamethylenediamine and Raney nickel catalyst, a nitroaromatic compound whereby the Raney nickel catalyst is passivated and catalytic decomposition of the hexamethylenediamine is substantially decreased.

7. The process improvement of claim 6 wherein the weight ratio of the nitroaromatic compound to the catalyst is 2–10.

8. The process improvement of claim 6 wherein the weight ratio of the nitroaromatic compound to the catalyst is 10.

9. The process improvement of claim 6 wherein the nitroaromatic compound is selected from the group consisting of nitrobenzene, dinitrobenzene and dinitrophenol.

10. The process improvement of claim 6 wherein the nitroaromatic compound is 2,4-dinitrophenol.

11. The process for the passivation of Raney nickel catalyst in a process discharge stream comprising an amine and Raney nickel catalyst so as to prevent decomposition of the amine during its recovery, the process comprising charging a nitroaromatic compound to the process discharge stream.

12. The process of claim 11 wherein the weight ratio of the nitroaromatic compound to the catalyst is 2–10.

13. The process of claim 11 wherein the weight ratio of the nitroaromatic compound to the catalyst is 10.

14. The process of claim 11 wherein the nitroaromatic compound is selected from the group consisting of nitrobenzene, dinitrobenzene and dinitrophenol.

15. The process of claim 11 wherein the nitroaromatic compound is 2-4-dinitrophenol.

16. The process of claim 11 wherein the nitroaromatic compound is charged to the process discharge stream under hydrogen pressure.

* * * * *